United States Patent [19]

Dockner et al.

[11] Patent Number: 4,803,283
[45] Date of Patent: Feb. 7, 1989

[54] PREPARATION OF 4(5)-NITROIMIDAZOLE-5(4)-CARBOXYLIC ACIDS

[75] Inventors: Toni Dockner, Meckenheim; Uwe Kempe, Dannstadt-Schauernheim; Hermann Koehler, Beindersheim, all of Fed. Rep. of Germany

[73] Assignee: BASF Aktiengesellschaft, Ludwigshafen, Fed. Rep. of Germany

[21] Appl. No.: 126,867

[22] Filed: Nov. 30, 1987

[30] Foreign Application Priority Data

Dec. 4, 1986 [DE] Fed. Rep. of Germany ....... 3641514

[51] Int. Cl.$^4$ .......................................... C07D 233/91
[52] U.S. Cl. .................................................. 548/339
[58] Field of Search ......................................... 548/343

[56] References Cited

U.S. PATENT DOCUMENTS 4,145,553  3/1979  Wetzler et al. ..................... 548/343

FOREIGN PATENT DOCUMENTS 2645172  4/1978  Fed. Rep. of Germany ...... 548/343

OTHER PUBLICATIONS

K. Hofmann, "The Chemistry of Heterocyclic Compounds", "Imidazole and Its Derivatives", Part I, 1953, p. 123.
J. Chem. Society, 115, 217-236 (1919).
Ca 51, 17897a, 1957.
Chem. Abstracts 82, 72,869f (1975).
Heterocyclic Compounds, vol. 5, p. 208, lines 5-10 (1957).
Chem. Abstracts 51, 1897a (1957).
Hofmann, Imidazole and Its Derivatives, Part I, Interscience Publishers, Inc. NY, (1953) p. 127.

*Primary Examiner*—John M. Ford
*Assistant Examiner*—Robert C. Whittenbaugh
*Attorney, Agent, or Firm*—John H. Shurtleff

[57] ABSTRACT

4(5)-nitroimidazole-5(4)-carboxylic acids are prepared by reacting an imidazole-4(5)-carboxylic acid with a mixture of sulfuric acid and nitric acid at not less than 80° C., the water content of the reaction mixture at the beginning of the reaction being no higher than 5% by weight, based on the reaction mixture.

14 Claims, No Drawings

PREPARATION OF 4(5)-NITROIMIDAZOLE-5(4)-CARBOXYLIC ACIDS

The present invention relates to a process for the preparation of 4(5)-nitroimidazole-5(4)-carboxylic acids.

While imidazoles can be nitrated in sulfuric acid by known processes, for example as described in German Laid-Open Application DOS No. 2,645,172, no corresponding conversion of imidazole-4(5)-carboxylic acids is described in the literature where temperatures higher than those conventionally used for the nitration of carbocyclic aromatics are used. Various authors even regard such a reaction as being impossible to carry out, for example K. Hoffmann in The Chemistry of Heterocyclic Compounds, Imidazole and Its Derivatives, Part I, 1953, Interscience Publishers, page 128, Paragraph 3. R. G. Fargher and F. L. Pyman too, in J. Chem. Soc. (1919) 115, 217–236, in particular page 220, state that the nitration of imidazoles is impossible if a carboxyl group is present on the imidazole ring.

Various expensive and involved methods have therefore been chosen for the preparation of 4(5)-nitroimidazole-5(4)-carboxylic acids, of which the method described by C. P. Kulev and R. N. Gireva in Appl. Chem. USSR (1957) 30, 858 and C. A. (1957) 51, 17897a, appears to be the most elegant one. In this method, 4-hydroxymethylimidazole is first nitrated at a low temperature with fuming $HNO_3$ in 98% strength $H_2SO_4$, and the hydroxymethyl group is then oxidized at a higher temperature. However, the disadvantage of the process is that the starting material is obtained by an involved synthesis which gives a poor yield, starting from fructose.

It is an object of the present invention to permit 4(5)-nitroimidazole-5(4)-carboxylic acids to be obtained in a simple manner and in good yields.

We have found that this object is achieved by a process for the preparation of 4(5)-nitroimidazole-5(4)-carboxylic acids, wherein an imidazole-4(5)-carboxylic acid is reacted with a mixture of sulfuric acid and nitric acid at not less than 80° C., the water content of the reaction mixture at the beginning of the reaction being no more than 5% by weight, based on the reaction mixture.

The reaction takes place according to the following equation:

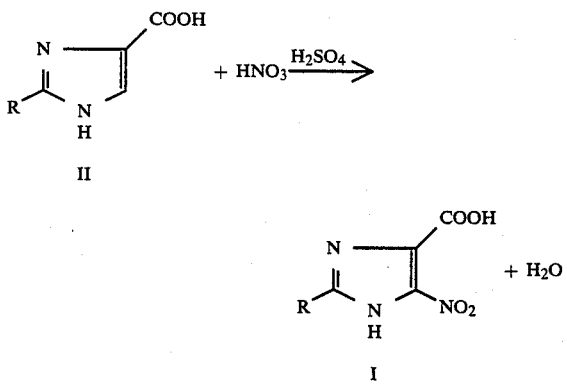

R is H or an aliphatic, cycloaliphatic, araliphatic or aromatic radical.

Suitable starting materials are imidazole-4(5)-carboxylic acids which are unsubstituted in the 2-position or substituted by an aliphatic, cycloaliphatic, araliphatic or aromatic radical. Examples of aliphatic radicals are alkyl of 1 to 20, in particular of 1 to 10, preferably 1 to 6, carbon atoms, eg. methyl, ethyl, n-propyl, isopropyl, n-butyl, sec-butyl or tert-butyl. Examples of cycloaliphatic radicals are $C_4$-$C_8$-cycloalkyl, eg. cyclohexyl or cyclopentyl. Examples of araliphatic radicals are aralkyl or alkylaryl, in particular of 7 to 12 carbon atoms, eg. benzyl, 2-phenylethyl, 3-phenylpropyl or 3-phenylbutyl. The phenyl radical advantageously carries a deactivating substituent. Aryl is, in particular, phenyl or substituted phenyl which advantageously contains deactivating groups as substituents, for example nitro groups, so that nitration of the aromatic is avoided. The stated radicals may furthermore carry substituents which are inert under the reaction conditions, for example $C_1$-$C_4$-alkyl, cyano, halogen or nitro. The starting materials are readily obtainable, for example, by the process described in German Laid-Open Application DOS No. 3,427,136.

The nitration of the imidazolecarboxylic acids or 2-substituted imidazolecarboxylic acids is carried out using nitric acid mixed with sulfuric acid, as a rule highly concentrated or fuming sulfuric acid (oleum). In general, a nitric acid having a density of from 1.38 to 1.52 (20° C.) and a sulfuric acid having a density of from 1.82 to 2.0 (20° C.) are used.

Nitric acid having a concentration of from 80 to 100% is particular advantageously used.

A ratio of from 0.1 to 1 mole of nitric acid per mole of sulfuric acid is advantageously chosen for the mixture of nitric acid and sulfuric acid, ie. the nitrating acid. As a rule, from 1 to 4, preferably from 1.5 to 2.5, moles of nitric acid are used per mole of imidazolecarboxylic acid II.

The water content of the reaction mixture before the beginning of the reaction should be no higher than 5% by weight, based on the reaction mixture. In general, the water content is from 0 to 2, in particular from 0 to 1, % by weight, based on the reaction mixture. The water of reaction formed during the nitration can advantageously be bound by adding $SO_3$ (oleum).

The reaction temperature is not less than 80° C. It may be varied within wide limits above this temperature but as a rule temperatures of from 80° to 200° C. are sufficient. Preferably, temperatures of from 80° to 180° C., in particular from 100° to 160° C., may be chosen.

The reaction can be carried out continuously or batchwise by the conventional techniques, as a rule under atmospheric pressure.

When the reaction is complete, which is generally the case after from 2 to 6 hours in the batchwise procedure, the products can be isolated in a conventional manner, for example by diluting the reaction mixture with ice or water, neutralizing the acid in the mixture with an alkali, preferably ammonia, until the pH reaches 2–5, and filtering off, washing and drying the precipitated end product. The 4(5)-nitroimidazole-5(4)-carboxylic acid thus obtained can be further purified by reprecipitation from water.

The products obtained by the novel process are useful intermediates for the synthesis of active compounds, in particular drugs and crop protection agents.

EXAMPLE 1

Preparation of 4(5)-nitroimidazole-4-carboxylic acid 112 g (1 mole) of imidazole-4(5)-carboxylic acid were introduced slowly into 553 g of 24% strength oleum while stirring, and 156 g of 81% strength HNO$_3$ were added dropwise at 100° C. in the course of 45 minutes. The reaction mixture was stirred for a further 5 hours at 100° C., cooled and poured onto 500 g of ice. Thereafter, the pH was brought to 3 with ammonia water, and the precipitate which separated out was filtered off under suction, washed and dried to give 163 g of crude 4(5)-nitroimidazole-5(4)-carboxylic acid having a purity of 67.5%, corresponding to a yield of 70%, based on imidazole-4(5)-carboxylic acid used.

The crude product was dissolved in aqueous NaOH at pH 11.5, after which the pH was brought to 10 with concentrated hydrochloric acid. The precipitated solid was filtered off and discarded. The nitrocarboxylic acid was then precipitated at pH 8, filtered off, washed and dried. In this way, the pure 4(5)-nitroimidazole-5(4)-carboxylic acid of melting point 301°-303° C. was obtained, the purity being >97%, (determined by high pressure liquid chromatography).

EXAMPLE 2

Preparation of 2-methyl-4(5)-nitroimidazole-5(4)-carboxylic acid 63 g (0.5 mole) of 2-methylimidazole-4(5)-carboxylic acid were reacted with 78 g of 81% strength HNO$_3$ in 276.5 g of 24% strength oleum by a method similar to that described in Example 1, and the reaction mixture was worked up as described above. The crude yield of 2-methyl-4(5)-nitroimidazole-5(4)-carboxylic acid was 60%.

The crude product was reprecipitated from water as described above. In this way, the pure 2-methyl-4(5)-nitroimidazole-5(4)-carboxylic acid of melting point 250°-252° C. was obtained, the purity being >99% (determined by high pressure liquid chromatography).

We claim:

1. A process for the preparation of a 4(5)-nitroimidazole-5(4)-carboxylic acid, which comprises reacting an imidazole-4(5)-carboxylic acid with a mixture of sulfuric acid and nitric acid at not less than 80° C., the water content of the reaction mixture at the beginning of the reaction being no more than 5% by weight, based on the reaction mixture.

2. The process of claim 1, wherein the water content of the reaction mixture at the beginning of the reaction is from 0 to 2% by weight, based on the reaction mixture.

3. The process of claim 1, wherein from 1 to 4 moles of nitric acid are used per mole of imidazole-4(5)-carboxylic acid.

4. The process of claim 1, wherein about 0.1-1 mole of nitric acid is used per mole of sulfuric acid.

5. The process of claim 1, wherein from 80 to 100% strength nitric acid is used.

6. The process of claim 1, wherein the reaction is carried out at from 100° to 160° C.

7. The process of claim 1, wherein the water content of the reaction mixture at the beginning of the reaction is from 0 to 1% by weight, based on the reaction mixture.

8. The process of claim 1, wherein the reaction is carried out at temperatures from 80° to 200° C.

9. The process of claim 1, wherein the reaction is carried out at temperatures from 80° to 180° C.

10. The process of claim 1, wherein from 1.5 to 2.5 moles of nitric acid are used per mole of imidazole-4(5)-carboxylic acid.

11. The process of claim 1, wherein oleum is added to the reaction mixture to bind the water of reaction formed during the nitration.

12. The process of claim 1, wherein the nitric acid has a density of from 1.38 to 1.52 (20° C.) and is used in a concentration of from 80 to 100% and in an amount of from 1 to 4 moles per mole of imidazole-4(5)-carboxylic acid and in a proportion of about 0.1-1 mole per mole of sulfuric acid.

13. The process of claim 12, wherein the water content at the beginning of the reaction is from 0 to 2% by weight, based on the reaction mixture.

14. The process of claim 13, wherein oleum is added to the reaction mixture to bind the water of reaction formed during the nitration.

* * * * *